United States Patent [19]

Sienkiewicz

[11] Patent Number: 5,656,012
[45] Date of Patent: Aug. 12, 1997

[54] SURGICAL RETRACTOR

[75] Inventor: Henry R. Sienkiewicz, Stamford, Conn.

[73] Assignee: United States Surgical Corporation, Norwalk, Conn.

[21] Appl. No.: 319,172

[22] Filed: Oct. 6, 1994

[51] Int. Cl.[6] .................................................. A61B 17/02
[52] U.S. Cl. .......................... 600/204; 600/201; 600/203; 600/208; 600/210; 600/215; 606/198
[58] Field of Search ................................ 600/201, 203, 600/206, 208, 209–210, 215, 37, 234, 204; 606/110, 198, 205, 206, 207; 604/105

[56] References Cited

U.S. PATENT DOCUMENTS

| | | | |
|---|---|---|---|
| 832,201 | 10/1906 | Kistler | 606/198 |
| 1,271,456 | 7/1918 | Flack | 606/198 |
| 1,275,520 | 8/1918 | Bell | 600/206 |
| 1,947,649 | 2/1934 | Kadavy | 600/203 |
| 3,495,586 | 2/1970 | Regenbogen | 606/198 |
| 4,190,042 | 2/1980 | Sinnreich . | |
| 5,080,088 | 1/1992 | Levahn | 600/206 |
| 5,113,846 | 5/1992 | Hiltebrandt . | |
| 5,195,506 | 3/1993 | Hulfish | 600/206 |
| 5,195,507 | 3/1993 | Bilweis . | |
| 5,235,966 | 8/1993 | Jamner . | |
| 5,275,610 | 1/1994 | Eberback | 606/198 |
| 5,279,539 | 1/1994 | Bohan et al. . | |
| 5,318,012 | 6/1994 | Wilk | 606/198 |
| 5,318,586 | 6/1994 | Ereren . | |
| 5,325,848 | 7/1994 | Adams et al. . | |
| 5,339,803 | 8/1994 | Mayzels et al. . | |
| 5,345,927 | 9/1994 | Bonutti . | |
| 5,351,679 | 10/1994 | Mayzels et al. . | |
| 5,358,496 | 10/1994 | Oritz et al. | 606/198 |
| 5,441,044 | 8/1995 | Tovey et al. | 600/234 |

OTHER PUBLICATIONS

V. Mueller & Co. Catalog, No. 65, p. 827, 1963.

Primary Examiner—Richard J. Apley
Assistant Examiner—Beverly M. Flanagan

[57] ABSTRACT

A surgical retractor is disclosed having a handle portion, an elongated body portion extending distally from the handle portion and including an outer tube, a fixed stabilizing member extending from a distal end of the outer tube and a pair of resilient bands pivotably connected to a distal end portion of the stabilizing member. An actuation mechanism is provided which is associated with the handle portion and proximal end portions of the bands for moving the bands between open and closed position. The surgical retractor further includes a sheath dimensioned to receive at least a portion of the stabilizing member and the bands.

27 Claims, 8 Drawing Sheets

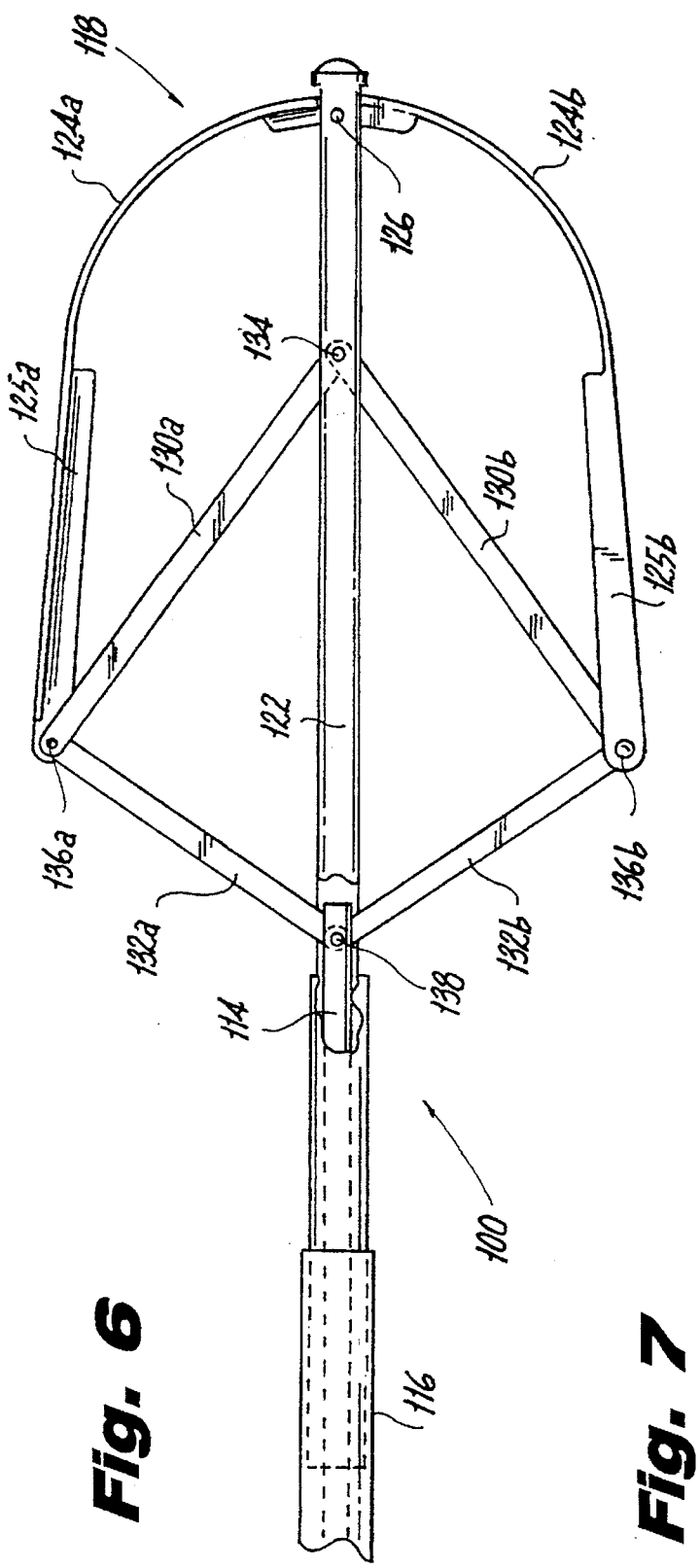

SURGICAL RETRACTOR

BACKGROUND

1. Technical Field

This application relates to surgical instrumentation, and more particularly, to a surgical retractor having an expandable sheath which defines a retraction surface for manipulating tissue and organs during endoscopic or laparoscopic surgical procedures.

2. Description of Related Art

In conventional surgical procedures the function of holding tissue and organs in a given location to facilitate access and viewing is typically accomplished by a retractor. The instrumentation is typically in the form of a broad paddle structure or multiple fingers attached to a handle. See, for example, U.S. Pat. No. 3,467,079 to James. One disadvantage of these methods is the requirement of making large incisions, often through major muscles, in order to manipulate the above instrumentation in the body cavity.

Endoscopic or laparoscopic procedures overcome many of the drawbacks of conventional surgery. Such procedures are characterized by the provision of an elongated cannula structure having a relatively small diameter with a proximal and distal end. The distal end is passed through the surrounding tissue into a body cavity via an incision in the body wall. The body cavity is typically inflated or "insufflated" with carbon dioxide gas to aid in viewing and accessing the surgical site. The cannula provides a conduit for insertion of surgical instrumentation into the cavity. These procedures allow for smaller incisions, shorter patient recovery periods and require less anesthesia than conventional methods.

Although the insufflation gas expands the abdomen to permit the surgeon to view the surgical site, it is often necessary to manipulate the internal organs or tissues to provide a clear path to the surgical objective. In the prior art, it has been known to utilize grasping tools which pull on the organs or tissues to move them out of the way to provide a clear visual path for the surgeon. However, these devices may damage the organs or tissues which they grasp, and consequently these devices are utilized only when absolutely necessary. In order to avoid the problems associated with grasping tools, endoscopic retractor mechanisms have been developed which are utilized to push and hold the tissue or organs away from the surgical site. Typically, these devices include paddles and/or fingers which expand after the retractor has been inserted into the abdomen through the trocar cannula. Such devices are disclosed in, for example, U.S. Pat. No. 4,654,028 to Suma, U.S. Pat. No. 4,909,789 to Taguchi et al., and U.S. Pat. No. 5,195,505 to Josefsen. Other retractor devices include collapsible fingers joined by webs of resilient material which expand to form the retractor. These devices are disclosed in, for example, U.S. Pat. No. 4,190,042 to Sinnreich and U.S. Pat. No. 4,744,363 to Hasson. Other devices include retractors having expandable frames for supporting expandable latex sheaths or covers, such as that described in U.S. Pat. No. 5,178,133 to Pena.

While one or more of the aforementioned devices have been successfully used in laparoscopic procedures, larger organs, such as the intestine and/or stomach, tend to be too large and too heavy to be properly supported by these retractors. Consequently, the retractors have difficulty in clearing the surgical field to provide access for the surgeon to the surgical site. Due to the small size of the instrumentation, particularly the trocar cannula through which these instruments must pass, it is difficult to provide a retractor mechanism which can support or otherwise manipulate large and pliable organs such as the intestines or stomach.

Therefore, a need exists for a retractor mechanism which may be utilized to manipulate large organs and that is reliable as far as the strength and durability of the instrument is concerned. A need also exists for a retractor instrument that can clear the surgical site of heavy organs and tissue, where the instrument is small in relation to the organ and can be utilized with conventional trocar cannulas to provide access to the site during an endoscopic or laparoscopic surgical procedure.

SUMMARY

A surgical retractor is provided that includes a stabilizing member defining a longitudinal axis and having a distal end portion, and at least one band or arm member having a end portion connected to the distal end portion of the stabilizing member or arm and movable between an open position and a closed position. The retractor preferably further includes a tubular sheath dimensioned to receive the stabilizing member and the band member, and is configured to expand when the band member is moved from the closed position to the open position. The surgical retractor is further provided with a mechanism for selectively moving the band member between the open position and the closed position.

In a preferred embodiment, the surgical retractor includes an elongated outer tube, two band members, or arms a stationary stabilizing member extending distally from a distal end of the outer tube, a sheath disposed about the band members and the stabilizing member and a mechanism for moving the band members between an open position and a closed position. The sheath is preferably fixed to the distal end of the outer tube and is expandable by manipulation of the band moving mechanism.

In use, the bands and sheath are collapsed and passed through a previously placed cannula in the body. An optional cover tube can be used to facilitate passage of the sheath through the cannula. Once the sheath and arms are disposed in the body cavity, the arm moving mechanism is manipulated to expand the arms and sheath. If a cover tube is used, the tube is withdrawn proximally prior to expansion. The combination of the arms, sheath and stabilizing member provide a retractor surface that can be used to manipulate organs or tissue. To withdrawn the device, the arms are collapsed and the instrument is pulled out of the cannula. Since the sheath is preferably flexible, the sheath is easily removed, i.e., without use of the optional cover tube. Alternatively, if a cover tube is used, the tube can be advanced distally over the sheath prior to removal.

BRIEF DESCRIPTION OF THE DRAWINGS

Various embodiments are described herein with reference to the drawings wherein:

FIG. 6 is a side elevational view of the retractor assembly of FIG. 5 in an open position, shown with the sheath removed;

FIG. 7 is a side elevational view of the retractor assembly of FIG. 5 in a substantially closed position, shown with the sheath removed;

DETAILED DESCRIPTION OF PREFERRED EMBODIMENTS

Figure 1:
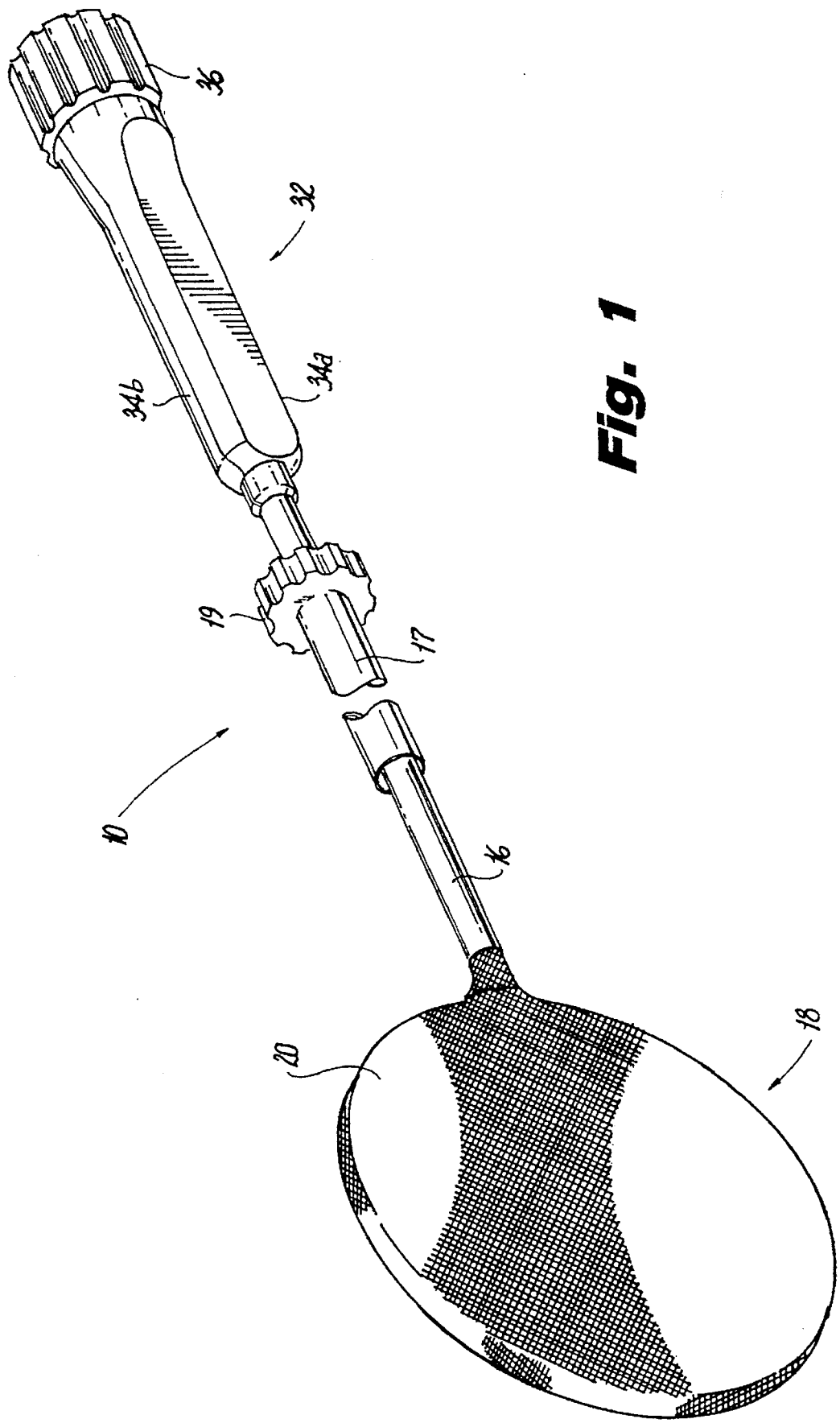
FIG. 1 is a perspective view of a surgical retractor constructed in accordance with a preferred embodiment and disposed in an open position.

In the drawings and in the description which follows, the term "proximal", as is traditional, will refer to the end of the apparatus which is closest to the operator, while the term "distal" will refer to the end which is furthest from the operator.

The present apparatus shall be discussed in terms of endoscopic procedures and apparatus. However, use herein of terms such as "endoscopic", "endoscopically", and "endoscopic portion", among others, should not be construed to limit the present disclosure to an apparatus for use only in conjunction with an endoscopic tube. To the contrary, it is believed that the present apparatus may find use in procedures wherein access is limited to a small incision including but not limited to endoscopic, arthroscopic and/or laparoscopic procedures.

Referring to FIG. 1, there is illustrated a unique surgical retractor constructed in accordance with a preferred embodiment designated generally by reference numeral 10. Surgical retractor 10 includes an elongated body portion which includes an outer tube 16 having proximal and distal end portions, an expandable retractor assembly 18 covered by an expandable tubular sheath 20 located at the distal end of tube 16, and a handle assembly 32 located at the proximal end of tube 16. The expandable retractor 18 is progressively deployed by an actuator mechanism that includes adjusting knob 36 provided at the proximal end portion of handle 32. Also shown in FIG. 1 is optional cover tube 17 disposed about outer tube 16. Cover tube 17 has gripping member 19 associated therewith to facilitate longitudinal (distal-proximal) movement along outer tube 16.

Figure 2:
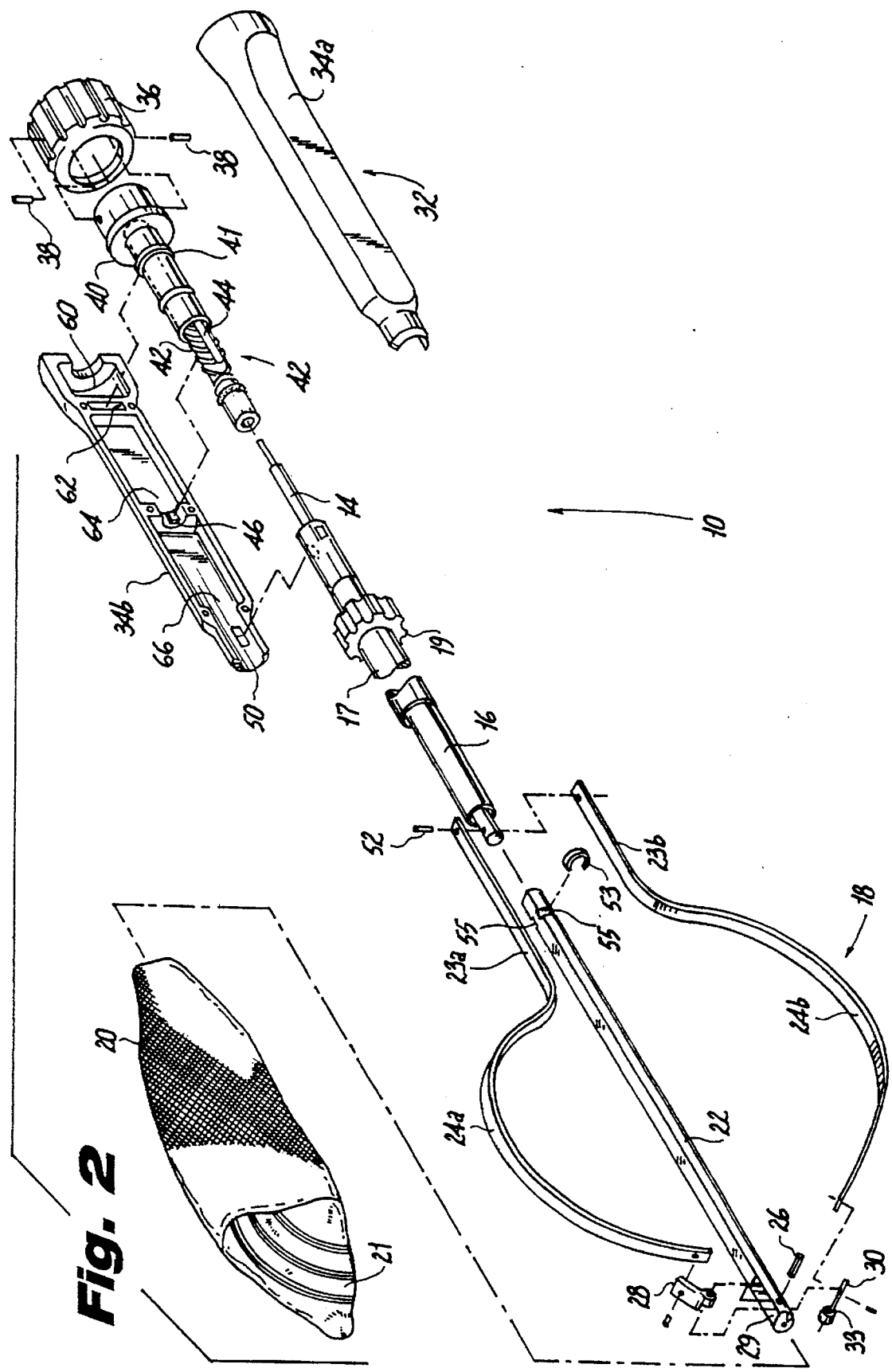
FIG. 2 is an exploded perspective view of the surgical retractor of FIG. 1.

Turning to FIG. 2, retractor assembly 18 consists of a stabilizing member (or center member) 22 oriented along a longitudinal axis which provides support to the retractor assembly 18 during the manipulation of organ structures or other body tissue. A distal end portion of the stabilizing member 22 is provided with a convex tip to inhibit puncturing of tubular sheath 20 and to prevent trauma to internal tissue and organs during insertion. A pair of resilient band members 24a and 24b are pivotably mounted at the distal end portion of stabilizing member 22 by hinge members 28 and 30, respectively attached to the distal end portions of the resilient bands 24a and 24b. Hinge members 28 and 30 are dimensioned to be received within slot 29 formed at the distal end portion of stabilizing member 22 and are pivotably retained therein by pivot pin 26 which passes through radial bore 31 formed in stabilizing member 22 and bores 33 in each hinge member. Proximal ends 23a and 23b of hinge members 28 and 30 are pinned by pin 52 to the distal end of rod 14, which is longitudinally slidable within outer tube 16.

Resilient bands 24a and 24b are preferably formed of stainless steel or other flexible resilient material, such as shape memory alloy or a flexible polymer, the configuration of which can be controlled mechanically by applying a stress to the material. In the present embodiment, the resilient bands are movable between an open, deployed configuration and a closed retracted position. In the deployed position, the shape of each of the resilient bands 24a and 24b is preferably an arcuate configuration. In the retracted position, resilient bands 24a and 24b are substantially straight and extend proximally from the distal pivotable hinge point and are in close approximation with stabilizing member 22 along the length of the resilient bands. The resilient bands 24a and 24b are preferably fabricated with a rectangular cross-section to strengthen the bands in the deployed position. Alternatively, the cross-section may be semicircular or other suitable configuration.

The expandable sheath 20 is preferably fabricated from a textile material such as surgical mesh, cloth, nylon, etc., and configured to enclose the stabilizing member 22 and the resilient bands 24a and 24b. Alternatively, sheath 20 can be fabricated from an elastomeric material such as, for example, latex. The proximal end of sheath 20 is preferably retained between locking collar 53 and proximal notches 55 formed on stabilizing member 22. When assembled, locking collar 53 and the proximal end of stabilizing member 22 are inserted into the distal end of outer tube 16 and are held in a fixed position relative to tube 16 by friction fit or other means, i.e., glue, pins or the like. Bands 24a and 24b are also disposed in sheath 20 and are slidable relative to the stabilizing member so as to permit expansion within the sheath. In the deployed position of the resilient bands as described hereinabove, sheath 20 is expanded so as to define a retracting surface for manipulating body tissue and organs during laparoscopic or endoscopic surgical procedure. Reinforcing ribs 21 may be provided in the sheath 20 to aid in resisting deformation or tearing of the retraction surface during surgical manipulation.

Figure 3:
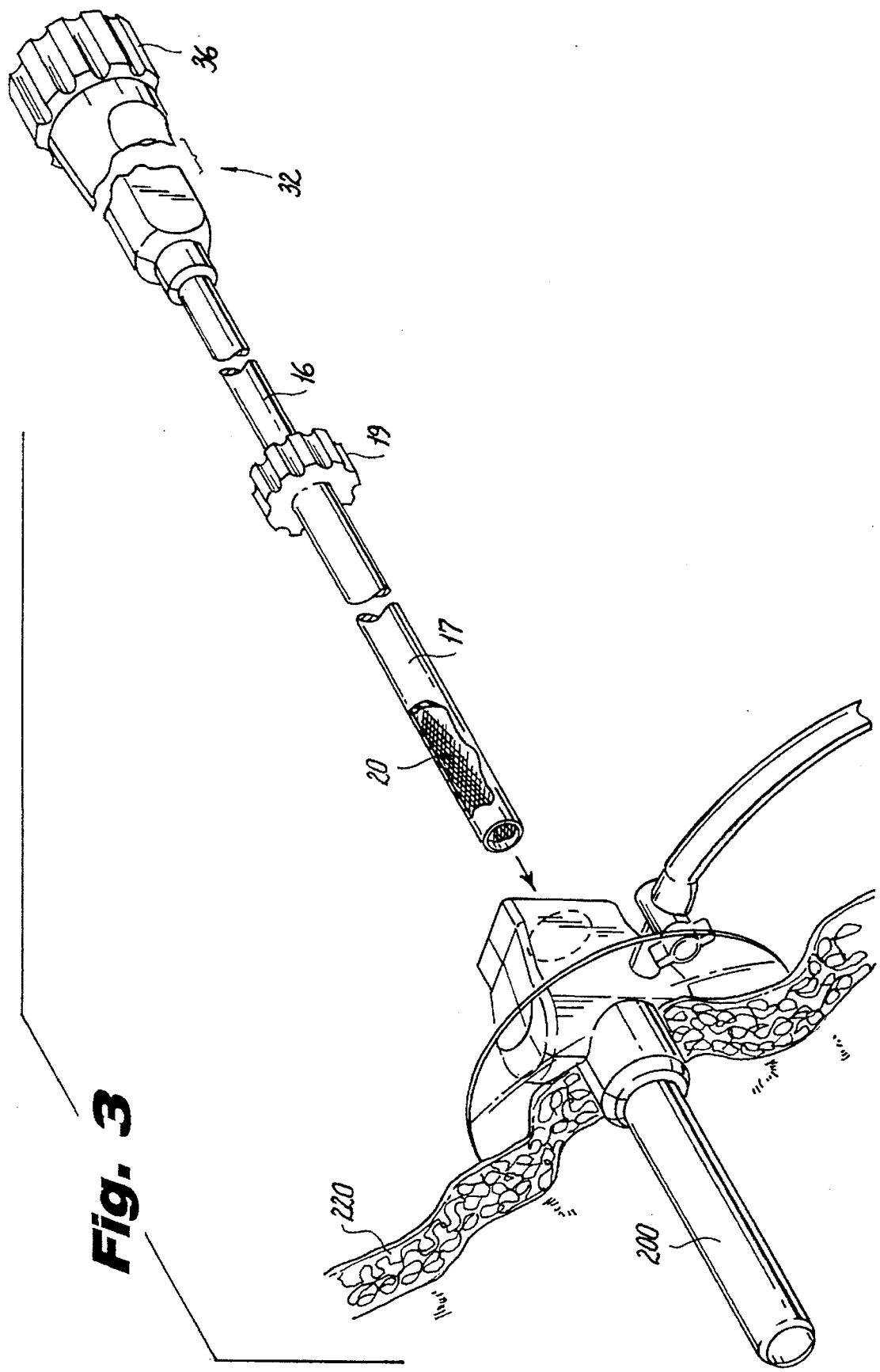
FIG. 3 is a perspective view of the surgical retractor of FIG. 1 in the closed position approaching a cannula.

When collapsed, retractor assembly 18 is dimensioned to be received within cover tube member 17 when the tube is advanced distally (see FIG. 3). The proximal end of cover tube 17 has grasping surface 19 to facilitate longitudinal movement of the tube.

With continued reference to FIG. 2, the handle portion 32 includes right and left hemi-sections 34a and 34b having a stepped longitudinal bore 50 extending therethrough defined by a proximal chamber 60, circumferential groove section 62, medial chamber 64, and distal chamber 66. Handle portion 32 houses an actuator mechanism for manipulating retractor assembly 18. The proximal portion of outer tube 16 is connected to the distal portion of handle 32 and the longitudinal bore of tube 16 is coaxial with longitudinal bore 50 of handle 32.

The actuator mechanism includes rotatable knob 36, rotatable screw housing member 40, and axially advanceable driving screw 42. The distal end of screw 42 is provided with a longitudinal bore for receiving the proximal end portion of driving rod 14 which is slidably received in outer tube 16. The distal end portion of driving rod 14 is connected to bands 24a and 24b by pin 52 as described above. Knob 36 is rigidly affixed to rotatable screw housing member 40 by retaining pin 38 and rotates coaxially therewith. Rotatable screw housing member 40 is formed with an internal threaded bore extending at least partially therethrough for operatively engaging driving screw 42. Screw housing member 40 is also formed with an annular mounting flange 41 dimensioned for engagement in the circumferential groove 62 of handle sections 34a and 34b. Driving screw 42 is preferably provided with a longitudinal slot 44 for accommodating a longitudinal engaging boss 46 formed within longitudinal bore 50 of handle section 34. The engagement of boss 46 in longitudinal slot 44 restrains driving screw 42 to longitudinal displacement only, such that axial rotation of the coupled knob 36 and rotatable screw member 40 effects corresponding longitudinal displacement of driving screw 42, driving rod 14. Longitudinal movement of rod 14 Controls the deployment of bands 24a and 24b within sheath 20. The function of displacing driving rod 14 distally may be alternatively performed by a sliding handle mechanism.

Figure 4:
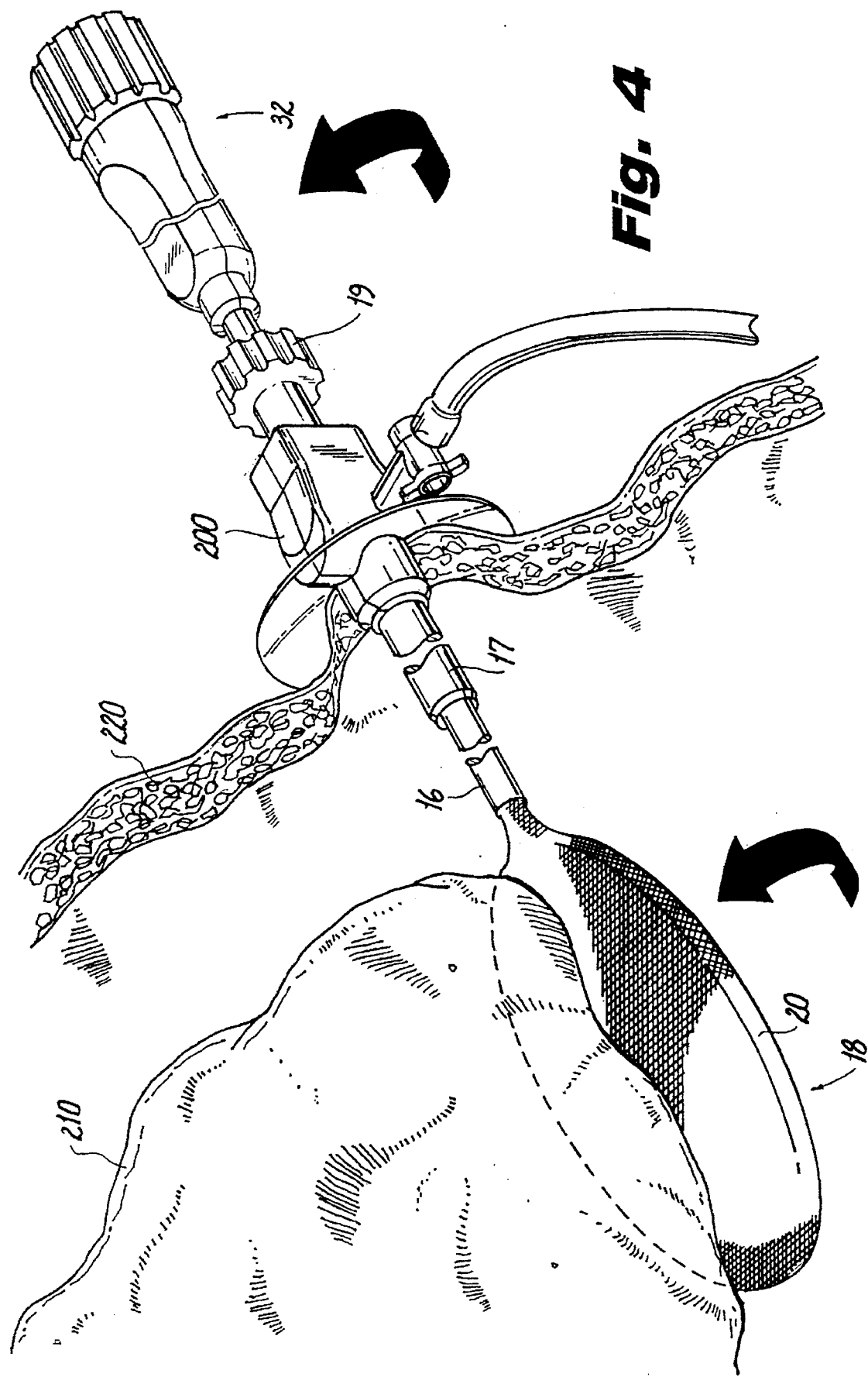
FIG. 4 is a perspective view of the surgical retractor disposed within a cannula in the body cavity.

Referring to FIGS. 3–4, use of retractor 10 is illustrated. Cannula 200 is inserted through body wall 220 at the operative site to access tissue or organs 210. In the retracted position illustrated in FIG. 3, stabilizing member 22, bands 24a and 24b and sheath 20 are disposed in cover tube 17. In this configuration, the distal end of instrument 10 can be easily inserted through cannula 200. Turning to FIG. 4, cover tube 17 has been slid proximally to expose retractor assembly 18. Knob 36 has been rotated to move center rod 14 distally thereby causing resilient bands 24a and 24b to move distally and expand within sheath 20. Distal movement of rod 14 terminates upon contact with the proximal end of stabilizing member 22.

During a typical laparoscopic or endoscopic surgical procedure, several trocar tubes 200 can be inserted to accommodate an endoscope for viewing and other instruments to carry out the procedure. Upon completion of the procedure, the surgeon can collapse retractor assembly 18 by rotating knob 36. Retractor 10 then may be withdrawn from the trocar. If cover tube 17 is used, it can optionally be advanced distally to cover assembly 18 prior to withdrawal.

Figure 5:
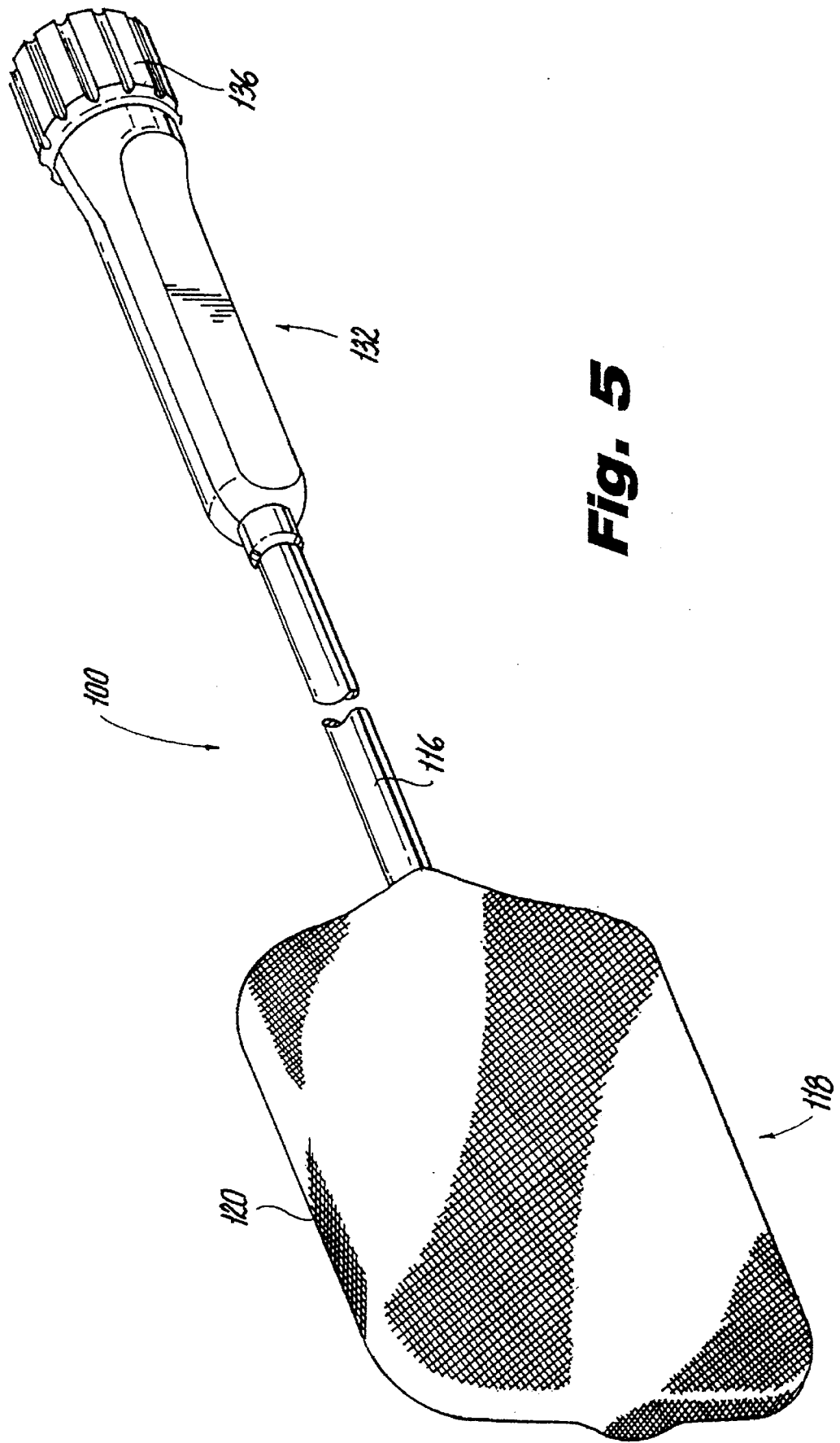
FIG. 5 is a perspective view of another preferred embodiment of a retractor assembly disposed in an open position.

In FIGS. 5–7, there is shown at 100 an alternative embodiment of a surgical retractor. Retractor 100 is utilized in a similar manner to retractor 10 heretofore described. Retractor 100 includes expandable retractor assembly 118 covered by expandable sheath 120, an elongate body portion which includes outer tube 116, and handle assembly 132. Similar to the previous embodiment adjusting knob 136 is provided at the proximal end portion of the handle 132 to deploy retractor assembly 118.

FIGS. 6–7 illustrate the structural configuration of surgical retractor 100. Retractor assembly 118 consists of a rigid stabilizing member 122 oriented along a longitudinal axis having a proximal end portion and a distal end portion. The proximal end of the stabilizing member 122 is dimensioned to be slidably received in outer tube 116. Retractor assembly 118 further consists of a pair of resilient bands 124a and 124b having strengthening ribs 125a and 125b, a pair of medial arms 130a and 130b, and a pair of proximal arms 132a and 132b.

The following description is referenced to one side of the retractor assembly 118, but is applicable to a retractor having a symmetrical configuration, as shown. Resilient band 124a is preferably formed from stainless steel, shape memory alloy or flexible polymer. In an unstressed state, resilient band 124a consists of a distal straight portion, a medial portion having a radiused elbow configuration, and a proximal straight portion. The distal portion of resilient member 124a is adapted to be pivotably mounted to the distal end portion of stabilizing member 122, and pivotably retained therein by distal retaining pin 126.

Medial arm 130a has a first end pivotably mounted to stabilizing member 122 and retained therein by a medial retaining pin 134, and a second end pivotably connected to the proximal end portion of resilient band 124a, and retained therein by juncture retaining pin 136a. Proximal arm 132a has a first end pivotably mounted to driving rod 114 and retained therein by proximal retaining pin 138. A second end of proximal arm 132a is pivotably connected at the juncture of medial arm 130a and the distal end portion of resilient band 124a and retained by juncture retaining pin 136a.

FIG. 7 illustrates the structural configuration of surgical retractor 100 in a collapsed position, wherein driving rod 114 is moved proximally to collapse the frame structure of retractor assembly 118. In this embodiment, distal pin 126 and medial pin 134 are fixed with respect to the stabilizing member. Proximal pin 138 is fixed with respect to driving rod 114. Juncture pin 136a traces an arcuate path with respect to proximal pin 138 and medial pin 134 respectively. Progressive deployment or opening of the retractor is achieved by distal displacement of driving rod 114. At the proximal most position of driving rod 114, as illustrated in FIG. 7, juncture pin 136a is positioned at the closest transverse distance to stabilizing member 122, placing retractor assembly 118 in the closed position. The proximal and media arms 130a–b and 132a–b are positioned substantially within a recess formed in the stablizing member. At the distalmost position of driving rod 114 as illustrated in FIG. 6, juncture pin 136a is at the furthest transverse distance from stabilizing member 122, placing retractor 118 in the fully deployed position. The proximal and medial arms 130a–b and 132a–b are positioned substantially entirely outside of the recess. At such a time, sheath 120 is fully expanded and defines a substantially rectangular manipulation surface suitable for manipulating body tissue as well as organs and vessels.

Figure 8:
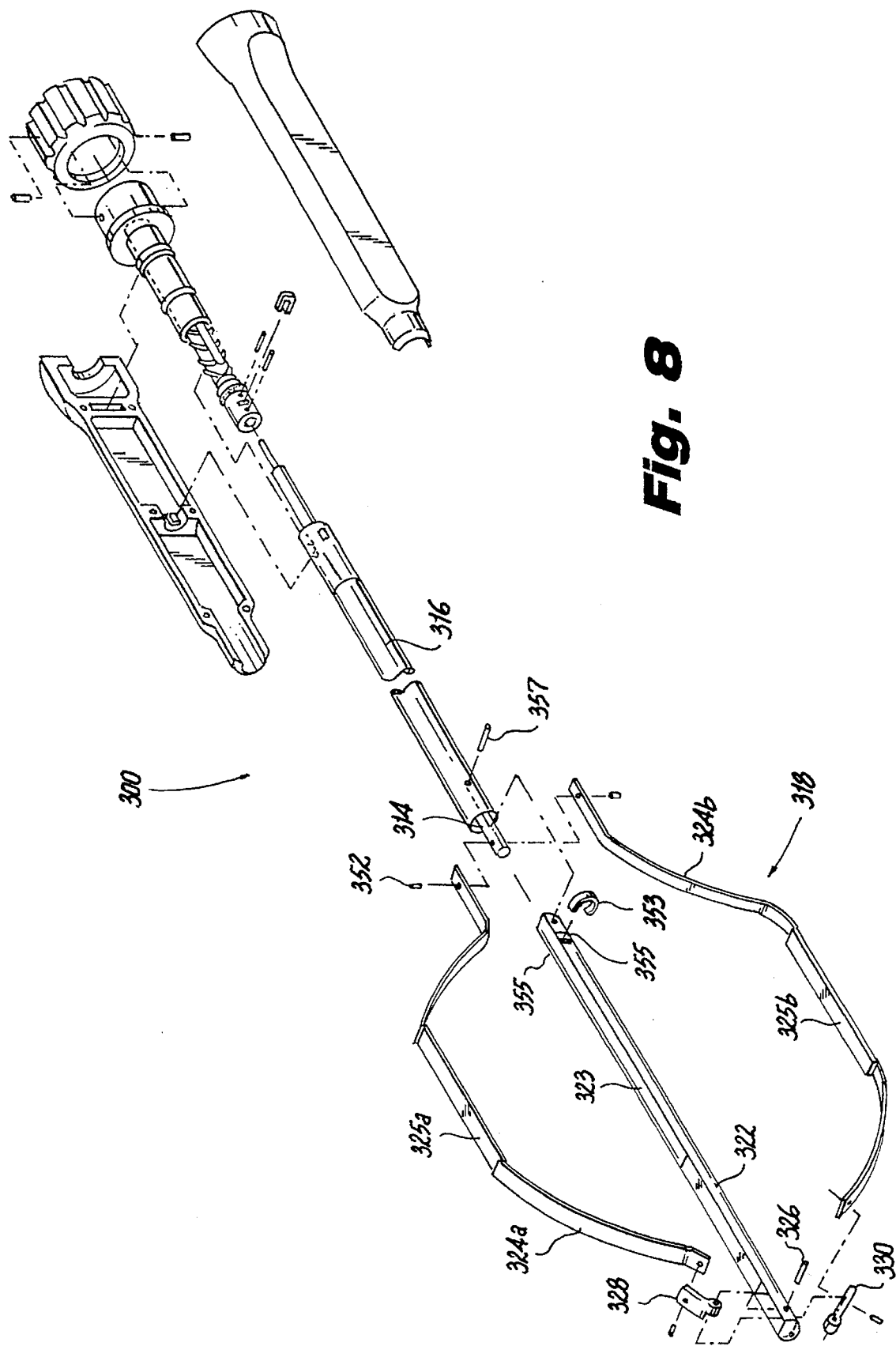
FIG. 8 is an exploded perspective view of a preferred embodiment of a surgical retractor without a sheath.
Figure 9:
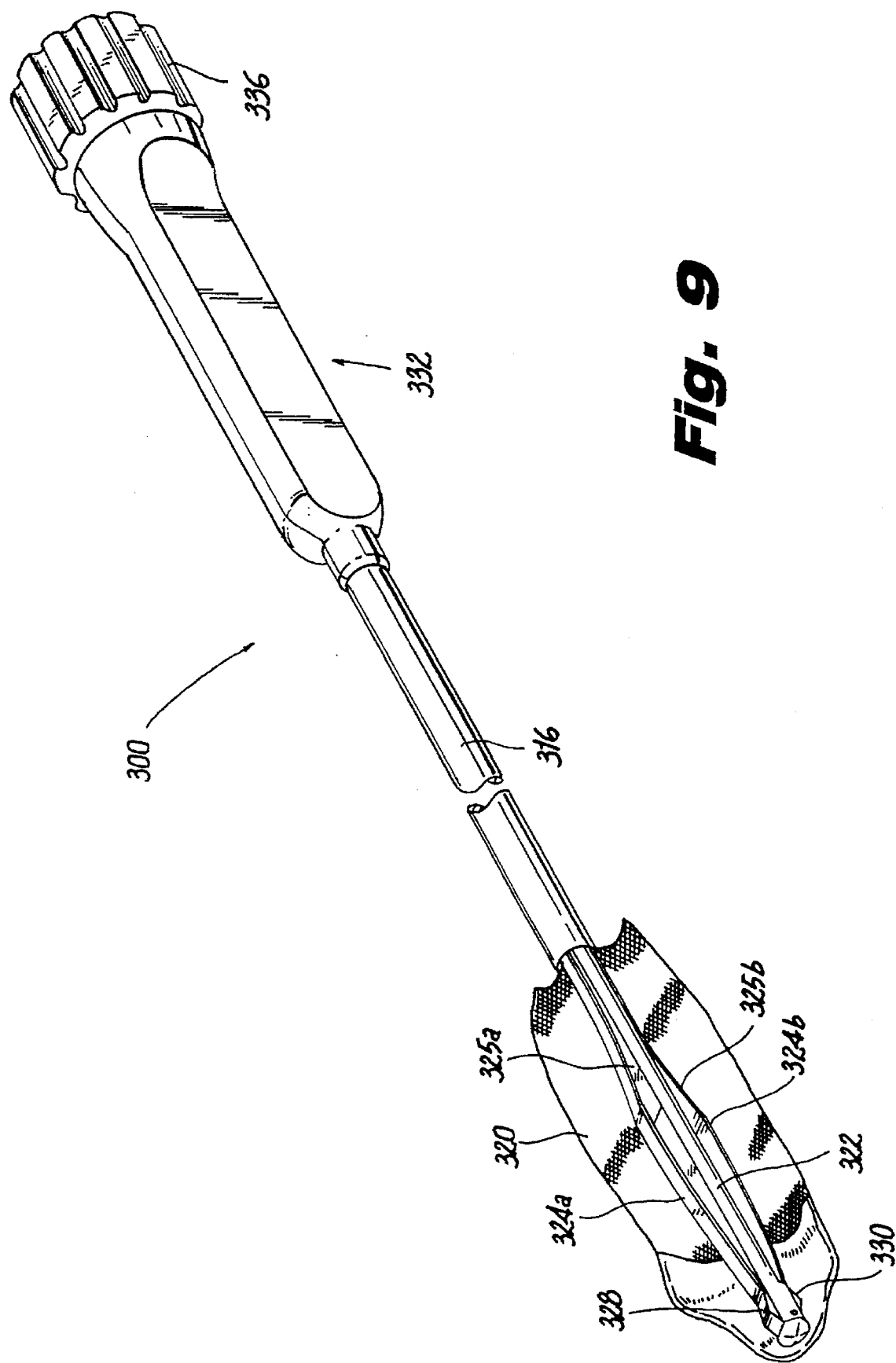
FIG. 9 is a perspective view of the retractor of FIG. 8 in a substantially closed position, shown with a substantially sheath partially cut away.

Turning to FIGS. 8–9, another preferred embodiment of the surgical retractor is shown. Retractor 300 is utilized in a similar manner to retractor 10 and 100 heretofore described. Retractor 300 includes expandable retractor assembly 318 covered by expandable tubular sheath 320, an elongate body portion which includes outer tube 316, and handle assembly 332. Expandable retractor 318 is progressively deployed by adjusting knob 336 provided at the proximal end portion of handle 332, similar to the manner described above.

Retractor assembly 318 includes a stabilizing member 322 depending longitudinally from outer tube 316 and fixed thereto with retaining pin 357. A pair of resilient bands 324a and 324b are pivotably connected at the distal portion of stabilizing member 322 by hinges 328 and 330, and retained therein by retaining pin 326. The resilient bands 324a and 324b are preferably formed of stainless steel or other resilient material. In the deployed configuration, the shape of resilient bands 324a and 324b is a substantially rectangular or trapezoidal configuration. Resilient bands 324a and 324b are provided at medial portions thereof with stabilizing rib members 325a and 325b. In the deployed configuration, rib members 325a and 325b are substantially parallel to stabilizing member 322 and are generally parallel with the longitudinal axis of the instrument. Rib members 325a and 325b provide resilient bands 324a and 324b with a deployed configuration that is predictable in shape and resists deformation during manipulation of heavy organs or tissue structures within the body cavity.

With continued reference to FIG. 8, the proximal end portions of resilient bands 324a and 324b are connected to the distal end of driving shaft 314 by retaining pin 352. Driving shaft 314 is configured for reciprocal longitudinal displacement within outer tube 316, and actuated by the actuator mechanism which includes knob 336, substantially as described hereinabove with respect to surgical retractor 10.

Attention is now directed to FIG. 9, which illustrates of retractor assembly 318 in the collapsed position. In the collapsed position, drive shaft 314 is in the proximal most position and resilient bands 324a and 324b in a substantial straightened, longitudinal position and at least partially disposed in outer tube 316. Stabilizing member 322 is further provided with a pair of channels 323 to receive stabilizing ribs 325a and 325b when the resilient bands 324a and 324b are in the collapsed configuration. Retractor 300 can also be provided with a slidable protective sleeve to surround the sheath during insertion and/or withdrawal from a cannula.

It will be understood that various modifications may be made to the embodiments disclosed herein. For example, the resilient bands may be oriented with respect to each other at greater or less than 180° resulting in a three dimensional retracting surface as surgical conditions require. Therefore, the above description should not be construed as limiting, but merely as exemplifications of preferred embodiments. Those skilled in the art will envision other modifications within the scope and spirit of the claims appended hereto.

What is claimed is:

1. A surgical retractor comprising:
   a handle portion;
   an elongated body portion extending distally from the handle portion, the body portion including an outer tube;
   a stabilizing member extending from a distal end of the outer tube, the stabilizing member having a recess;
   a pair of resilient bands having distal end portions pivotably connected to a distal end portion of the stabilizing member and having proximal end portions, the bands movable between a first position and a second position;
   an actuation mechanism at least partially disposed in the handle portion and operatively associated with the proximal end portions of the bands for moving the bands relative to the stabilizing member between the first position and the second position;
   a linkage operatively associated with the proximal end portion of the bands and the actuation mechanism in order to facilitate displacement of the bands to the open position, the linkage being located substantially within the stabilizing member recess in the first position and being located substantially entirely outside of the recess in the second position; and
   a sheath dimensioned to receive at least a portion of the stabilizing member and the bands.

2. The surgical retractor as recited in claim 1, wherein the body portion further includes an inner rod member slidably disposed within the outer tube, the proximal end portions of the bands being attached to and movable with the inner rod member in response to the actuation mechanism.

3. The surgical retractor as recited in claim 2, wherein the actuation mechanism includes a rotatable knob disposed on the handle member, the knob being operatively connected to a drive screw member disposed in the handle member, wherein rotation of the knob causes longitudinal movement of the inner rod member.

4. The surgical retractor as recited in claim 1, wherein the bands at least partially define an arcuate configuration in the open position.

5. The surgical retractor as recited in claim 1, wherein the bands include supporting ribs.

6. The surgical retractor as recited in claim 1, further comprising a cover tube slidably disposed on the body portion for receiving at least portions of the stabilizing member, the resilient bands and the sheath.

7. The surgical retractor as recited in claim 1, wherein a proximal portion of the sheath is fixedly connected to the distal end of the body portion.

8. The surgical retractor as recited in claim 1, wherein the sheath is formed of a woven material.

9. The surgical retractor according to claim 1, wherein the sheath is formed of an elastomeric material configured to expand when the bands are moved from the first position to the second position.

10. A surgical retractor comprising:
    a handle portion having an actuator at least partially disposed therein;
    an elongated body portion extending from the handle portion, the body portion including an inner rod member slidable within an outer tubular member in response to the actuator;
    a center member extending from a distal end portion of the outer tubular member;
    a pair of bands having distal end portions pivotably connected to a distal end portion of the center member, the pair of bands movable relative to the center member in response to movement of the actuator between a retracted position in which the bands are substantially aligned with the center member and an expanded position in which the bands are spaced from the center member, each band having an elongated stabilizing rib extending along at least a portion of the length of the band, the stabilizing rib substantially preventing flexure of the portion of the length of the band during movement between the retracted and expanded positions; and
    a sheath receiving at least portion of the center member and bands.

11. The surgical retractor as recited in claim 10, wherein the bands are more flexible than the center member.

12. The surgical retractor as recited in claim 10, wherein the sheath defines a substantially arcuate configuration in the expanded position and a substantially straightened position in the retracted position.

13. The surgical retractor as recited in claim 10, wherein the bands include supporting ribs on at least a medial portion thereof.

14. The surgical retractor as recited in claim 10, wherein the sheath is fixedly secured at a distal end of the body portion.

15. The surgical retractor as recited in claim 14, further comprising a cover tube slidably disposed on the body portion for receiving proximal portions of the center member, the bands and the sheath.

16. A surgical retractor comprising:
    a handle portion;
    an elongated body portion extending distally from the handle portion;
    a stabilizing member disposed at a distal end portion of the body portion;
    a pair of resilient bands having distal end portions pivotably connected to a distal end portion of the stabilizing member, the bands movable between a closed position, at least one intermediate position, and an open position, the bands being configured to form a predetermined geometric shape defining a first surface area when in the intermediate position, and forming a substantially similar predetermined geometric shape defining a second surface area when in the open position, the second surface area being greater than the first surface area, each band having a strengthening rib extending along a portion of its length, the strengthening rib being perpendicularly oriented with respect to the band;

an actuation mechanism associated with the handle portion for moving the bands relative to the stabilizing member between the closed position, the intermediate position, and the open position; and a sheath dimensioned to receive at least a distal portion of the stabilizing member and the bands.

17. The surgical retractor according to claim 16, wherein the body portion includes an outer tube member and an inner rod member slidably disposed therein, a proximal portion of the pair of bands being movable with the inner rod member in response to the actuation mechanism.

18. The surgical retractor comprising:

(a) a handle portion;

(b) an elongated body portion extending distally from the handle portion;

(c) a stabilizing member disposed adjacent a distal end portion of the body portion;

(d) a pair of resilient bands having distal portions pivotably connected to a distal end portion of the stabilizing member and having proximal end portions, the bands each having a stabilizing rib and being movable between a first position in which the pair of bands are in substantial alignment with the stabilizing member and a second position in which the bands are symmetrical about the stabilizing member and together have a substantially rectangular configuration, the stabilizing ribs each extending along a respective sidewall of the rectangular configuration and;

(e) an actuation mechanism associated with the handle portion for moving the bands relative to the stabilizing member between the first position and the second position.

19. A surgical retractor as recited in claim 18, wherein the actuation mechanism is an axial drive screw member.

20. A surgical retractor as recited in claim 18, wherein the body portion encloses at least the proximal end portion of the bands.

21. A surgical retractor as recited in claim 18, wherein a proximal portion of the sheath is fixedly connected to the distal end of the body portion.

22. A surgical retractor as recited in claim 18, further comprising a cover tube slidably disposed on the body portion for receiving at least portions of the stabilizing member, the resilient bands and the sheath.

23. A surgical retractor comprising:

(a) a handle portion;

(b) an elongated body portion extending distally from the handle portion;

(c) a stabilizing member disposed adjacent a distal end portion of the body portion;

(d) a pair of resilient bands having distal portions pivotably connected to a distal end portion of the stabilizing member and having proximal end portions, the bands movable between a first position and a second position, each band having a longitudinally extending stabilizing rib;

(e) an actuation mechanism associated with the handle portion configured to move at least one of the stabilizing member and the bands for moving the bands relative to the stabilizing member between the first position and the second position;

(f) a sheath dimensioned to receive at least a portion of the stabilizing member and the bands.

24. A surgical retractor as recited in claim 23, wherein the actuation mechanism is an axial drive screw member.

25. A surgical retractor as recited in claim 23, wherein the body portion encloses at least the proximal end portion of the bands.

26. A surgical retractor as recited in claim 23, wherein a proximal portion of the sheath is fixedly connected to the distal end portion of the body portion.

27. A surgical retractor as recited in claim 23, further comprising a cover tube slidably disposed on the body portion for receiving at least portions of the stabilizing member, the resilient bands and the sheath.

* * * * *